United States Patent
Stuck et al.

(10) Patent No.: US 9,592,646 B2
(45) Date of Patent: Mar. 14, 2017

(54) PHARMACEUTICAL TABLETS WITH DIFFRACTIVE MICROSTRUCTURE AND COMPRESSION TOOLS FOR PRODUCING SUCH TABLETS

(75) Inventors: Alexander Stuck, Wettingen (CH); Harald Walter, Horgen (CH); Marc Schnieper, Onex-Genéve (CH); Jürgen Söchtig, Wettswil (CH); Christian Zschokke, Basel (CH)

(73) Assignee: CSEM CENTRE SUISSE D'ELECTRONIQUE ET DE MICROTECHNIQUE SA, Neuchatel (CH)

( * ) Notice: Subject to any disclaimer, the term of this patent is extended or adjusted under 35 U.S.C. 154(b) by 1266 days.

(21) Appl. No.: 12/308,484

(22) PCT Filed: Jun. 12, 2007

(86) PCT No.: PCT/IB2007/052216
§ 371 (c)(1),
(2), (4) Date: Jan. 25, 2010

(87) PCT Pub. No.: WO2007/144826
PCT Pub. Date: Dec. 21, 2007

(65) Prior Publication Data
US 2010/0143467 A1    Jun. 10, 2010

Related U.S. Application Data (60) Provisional application No. 60/812,967, filed on Jun. 13, 2006, provisional application No. 60/812,957, filed on Jun. 13, 2006.

(30) Foreign Application Priority Data

Jan. 12, 2007  (CH) ..................................... 0042/07
Jan. 12, 2007  (CH) ..................................... 0043/07

(51) Int. Cl.
*A61K 9/20*   (2006.01)
*B30B 15/06*  (2006.01)
*A61J 3/10*   (2006.01)
*A61J 3/00*   (2006.01)

(52) U.S. Cl.
CPC ............ *B30B 15/065* (2013.01); *A61J 3/007* (2013.01); *A61J 3/10* (2013.01); *A61K 9/2072* (2013.01); *A61K 9/2095* (2013.01)

(58) Field of Classification Search
CPC ...... A61K 9/20; A61K 9/2072; A61K 9/2077; A61K 9/2095

USPC ................................................. 424/464, 467
See application file for complete search history.

(56) References Cited

U.S. PATENT DOCUMENTS

| | | | |
|---|---|---|---|
| 4,668,523 A | 5/1987 | Begleiter | |
| 5,451,505 A | 9/1995 | Dollinger | |
| 6,455,157 B1 | 9/2002 | Simons | |
| 2004/0163441 A1 | 8/2004 | Sawitowski | |
| 2005/0232130 A1 | 10/2005 | Oyake et al. | |
| 2006/0068006 A1* | 3/2006 | Begleiter ............. | A61K 9/2886 424/464 |
| 2010/0297027 A1* | 11/2010 | Loiret-Bernal ...... | A61K 9/2072 424/10.2 |

FOREIGN PATENT DOCUMENTS

| EP | 1 357 433 A2 | 10/2003 | |
|---|---|---|---|
| WO | WO 01/10464 A1 | 2/2001 | |
| WO | WO 2006027688 A1 * | 3/2006 | ........... A61K 9/2072 |
| WO | WO 2006/047695 A2 | 5/2006 | |
| WO | WO 2006047695 A2 * | 5/2006 | |

OTHER PUBLICATIONS

K. Marshall, "Tablet Press Fundamentals," *Tablets & Capsules* 2005 (p. 1-46).
N.A. Armstrong, "Considerations of Compression Speed in Tablet Manufacture," *Pharmaceutical Technology*, Sep. 1990, (6 pages).
European Office Action dated Apr. 9, 2013 for corresponding European Application No. EP 07766722.8.
Schnieper, M. et al; A New Way to Understand Zero Order Pigments; CSEM Scientific and Technical Report 2009.

* cited by examiner

*Primary Examiner* — Micah-Paul Young
(74) *Attorney, Agent, or Firm* — Young & Thompson (57) ABSTRACT

A tablet for pharmaceutical use has on at least one part of its surface a diffractive microstructure which generates diffraction effects which can be perceived in the visible spectral range and which serve as visual safety feature. The tablet includes a plurality of individual powder particles, where the diffractive microstructures are impressed into the surface of the individual powder particles. A compression tool to produce such tablets has on one pressing surface of the compression tool micro-structures, where the microstructures have dimensions which are smaller than the dimensions of the individual crystallites of the material of the pressing surface of the compression tool. The micro-structures of the compression tool can be produced for example by ion etching or by imprinting.

9 Claims, 9 Drawing Sheets

PHARMACEUTICAL TABLETS WITH DIFFRACTIVE MICROSTRUCTURE AND COMPRESSION TOOLS FOR PRODUCING SUCH TABLETS

BACKGROUND OF THE INVENTION

Field of the Invention

This invention relates to a tablet having an optical security feature formed as a diffractive micro-structure, a compression die for producing such tablets and a method for producing such tablets.

Discussion of Related Art

Counterfeit and gray market products and illegal re-imports are a major problem for pharmaceutical drugs. Drugs and medicines are counterfeited to an ever increasing extent, which is a problem not only in developing countries, where counterfeit products in the supply chain often amount to more than 50%, but this problem also exists in industrial countries where the prices of pharmaceutical drugs are often much higher. The prices for AIDS drugs or cancer drugs are often reduced significantly in developing countries, for example, for social reasons, but this increases the risk of abusive re-importing of these drugs into industrial nations.

To prevent abuse, packages of pharmaceutical drugs are provided with counterfeit-proof features. Holograms, optically variable inks, fluorescent dyes, special printing techniques such as microprinting and other security features are attached to the package with adhesive labels, are laminated onto the box or are applied directly to the package. One main disadvantage of such labeling is that it can be removed from the product or package and then reused or analyzed. Some companies apply security features to the sealing film of blister packs, but these have the same disadvantages.

Methods of applying counterfeit-proof signatures, such as DNA of a known sequence, U.S. Pat. No. 5,451,505, for example, molecules with a characteristic isotope composition or microparticles with a characteristic color layer sequence, U.S. Pat. No. 6,455,157, for example, are extremely critical because these signatures are taken together with the drug. For this reason, approval authorities such as the U.S. Food and Drug Administration (FDA) have not yet given approval for such methods.

Some attempts to apply a hologram to edible products have been published. PCT International Publication WO 01/10464 A1 discloses the coating of edible products with a thermally moldable and embossable layer. However, the application of this layer alters the composition and the production process of pharmaceutical pills, so it requires a new official approval. In addition, heating during the thermal shaping steps is problematical for many active ingredients.

U.S. Pat. No. 4,668,523 describes another approach in which a polymer solution is brought in contact with a mold having a diffractive relief. Then the polymer is hardened by drying. This step can be accelerated by heating. At the end, the hardened, edible polymer product carries the diffractive relief. This method is limited to polymer solutions and is very slow. In addition, the heating of the active ingredients used for the production of pharmaceutical tablets is again problematical. These disadvantages have prevented the market introduction of these techniques.

SUMMARY OF THE INVENTION

One object of this invention is to provide a tablet having an integrated security feature, the tablet having essentially the same composition as a traditional tablet which can be produced without elevated temperatures during the manufacturing process and which does not require an extension of the production process in comparison with the traditional methods. Another object of this invention is to provide a compression die with which such tablets can be produced as well as methods for producing such molds.

The term "tablet" in this context is understood to refer not only to tablets and pills intended for swallowing, sucking, chewing or dissolving in the mouth, but also other medicinal dosage forms such as suppositories or products that are dissolved in liquids before being taken. Besides pharmaceutical tablets, this is also understood to include non-pharmaceutical products such as bonbons or sweetener tablets.

These and other objects are achieved by a tablet, a compression die and by methods for manufacturing such compression dies according to the specification and the claims.

A tablet according to this invention has on its surface a diffractive microstructure, which creates perceptible diffraction effects in the optical spectral range and thus functions as a security feature. The microstructured surface may also be macroscopically structured to form, for example, logos, brand names, etc. The security feature cannot be removed from the tablet and also cannot be transferred subsequently to counterfeit products. To produce such tablets, an inventive compression die including one compression mold and two compression rams is used. The surface of the compression mold and/or one or both compression rams facing the powder mixture to be compressed each has a diffractive microstructure, which is formed during the compression operation, more precisely during the compression and compaction process, on the surface of the powder particles, thus forming a permanent diffractive microstructure on the surface of the finished tablet.

The traditional temperatures, pressures and process speeds of known tablet presses can be retained in producing the inventive tablets. In particular, a compression time of much less than 100 ms per tablet is sufficient. The inventive molds may be used in traditional tableting machines. Production of the inventive tablets is thus compatible with the existing and qualified tablet production methods and is thus inexpensive.

BRIEF DESCRIPTION OF THE DRAWINGS

This invention is explained in greater detail below with reference to drawings, wherein.

DETAILED DESCRIPTION OF THE INVENTION

Powder Mixtures for Pharmaceutical Tablets

Most tablets are produced by pressing a powder mixture in a compression mold. If active powders and fillers are merely mixed and then pressed directly to form tablets, it relates to direct tableting. This process is mainly a high-pressure molding process.

The mixture to be pressed comprises particles of different sizes, where the size distribution of the particles is critical for the tablet pressing process. Table 1 shows an example of a typical mixture including excipients for production of a pharmaceutical tablet. Table 2 shows the respective typical particle size distribution.

TABLE 1

| Amount wt % | Substance |
|---|---|
| 72.75 | lactose monohydrate |
| 24.25 | microcrystalline cellulose |
| 1.00 | Aerosil (colloidal silica, dried) |
| 1.00 | magnesium stearate |
| 1.00 | sodium salicylate (example of an active ingredient) |

TABLE 2

| Diameter of particles in μm | Amount in wt % |
|---|---|
| <75 | 15-25 |
| 75-150 | 30-50 |
| 150-250 | 15-25 |
| 250-500 | 5-15 |
| >500 | <2 |

Lactose and cellulose are the most widely used binders and fillers in direct tableting processes. These substances are especially suitable when provided with a diffractive microstructure.

The powder is transported by gravity in the tablet press equipment. Thus, a good free-flowing property is obligatory. Aerosil improves powder flow.

Magnesium stearate is used as a lubricant. Lubricants function by being distributed over the surface of the powder. They reduce the frictional forces between the powder and the compression dies and thus prevent the tablet from adhering to the compression die.

Decomposition active ingredients may be added to the powder mixture to improve decomposition, such as dissolution in water. The decomposition time of pills is typically measured in water at 37° C.

Sometimes a dye is added, but only a few dyes are allowed for use in medication. Practically all pharmaceutical tablets are thus a dull white. Some are bright red or light blue. Thus, all the tablets produced by the direct tableting process have a luminous and/or light-scattering surface.

Particles larger than 500 μm and/or smaller than 75 μm are critical for the compressing operation. The former reduce the mechanical stability of the pressed tablet while the latter are problematical for particle flow during the filling of the cavity of the compression die. Thus, the amount of these particles must be kept as low as possible. On the whole, it can be concluded that practically all powder particles used in the tablet pressing process are much larger than the diffractive microstructures, which are typically structures smaller than 5 μm in size and are created in the surface.

To prevent an unwanted chemical change in the ingredients during the production of the tablets, the temperature should advantageously be 50° C., or even better 40° C. The temperature is preferably between 15° C. and 35° C., such as room temperature.

Parameters of the Diffractive Microstructures

Figure 2:
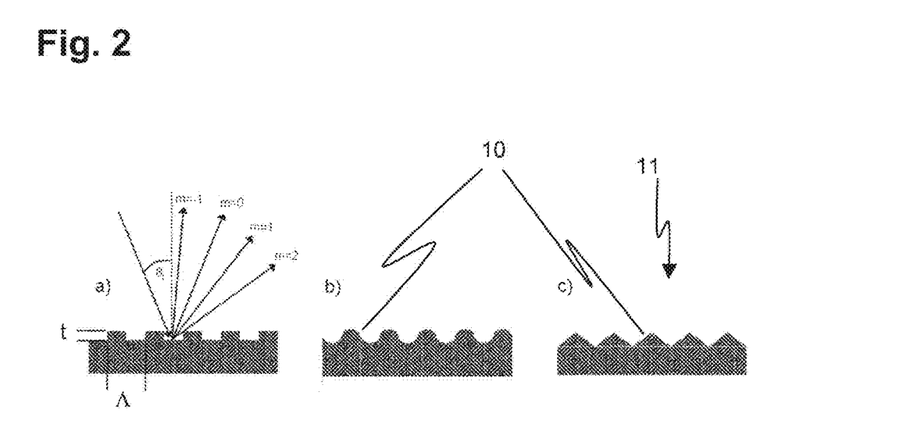
FIG. 2 shows a schematic cross section taken through diffractive microstructures on the surface of tablets produced with the method of this invention, with (a) rectangular, (b) sinusoidal and (c) triangular grating lines.

It is difficult to reliably and permanently create typical diffractive microstructures with a period $\Lambda$ of approx. 1-2 μm and a depth t on the order of 200-300 nm in the surface of a tablet, as illustrated in FIG. 2, for example, and reliably maintain them during the direct tableting process. These powder mixtures are naturally not intended for microstructuring and the size of the microstructures is much smaller than the dimension of the particles. For this reason, the surface of the particles themselves must be microstructured. Finally, the tableting process is ultimately not so fast that the time for microstructuring is extremely short. To be able to achieve this, certain parameters of the diffractive microstructure must be optimized, in particular the diffractive microstructure on the die surface, which acts as an embossing pattern. The parameter ranges of the microstructures for the inventive tablets which have been found particularly suitable are summarized in Table 2a.

TABLE 2a

| Parameter | Suitable range | Preferred range | Especially preferred range |
|---|---|---|---|
| Period $\Lambda$ | 300-5000 nm | 800-2500 nm | 1200-2500 nm |
| Depth t | 80-1000 nm | 100-500 nm | 150-300 nm |
| Shape | rectangular, sinusoidal, triangular or rounded shapes | sinusoidal or rounded shapes | sinusoidal or rounded shapes |

It is a challenge in the tableting process to prevent the diffractive microstructures that protrude out of the surface of the inventive tablet from being broken off. Microstructures including linear grating lines (1d grating) are more suitable than spot gratings (2d gratings) because the lines have a greater mechanical stability than the spots. Crossed gratings in the form of a hole grating are equally suitable in view of the stability of the connected grating lines.

The microstructuring increases the surface area of the compression die and thus increases the contact area between the compression die and the pressed tablet. This results in increased adhesion and thus may interfere with the separation of the finished tablet from the mold. To minimize this effect, the microstructure advantageously has a rounded or triagonal shape, such as a sinusoidal grating (FIG. 2(b), 2(c)). Microstructures having perpendicular walls, as illustrated in FIG. 2(a), are less ideal. In addition, the depth t of the microstructures should be as low as possible. However, a minimum depth t of approx. 80 nm is required for a visible diffractive effect. The diffraction efficiency of a sinusoidal grating is at its maximum, for example, when the grating depth corresponds to 0.3-0.4 grating periods. In addition, the microstructure must be deeper than the lubricant layer between the surface and the compression die or the wall of the compression mold and the tablet mass. Most lubricants have a laminar structure with sliding planes running slightly parallel to the surface of the compression die or the compression mold. For this reason, microstructures introduced into only this lubricant layer are easily broken off.

Producing Tablets with Diffractive Microstructures

Figure 1:
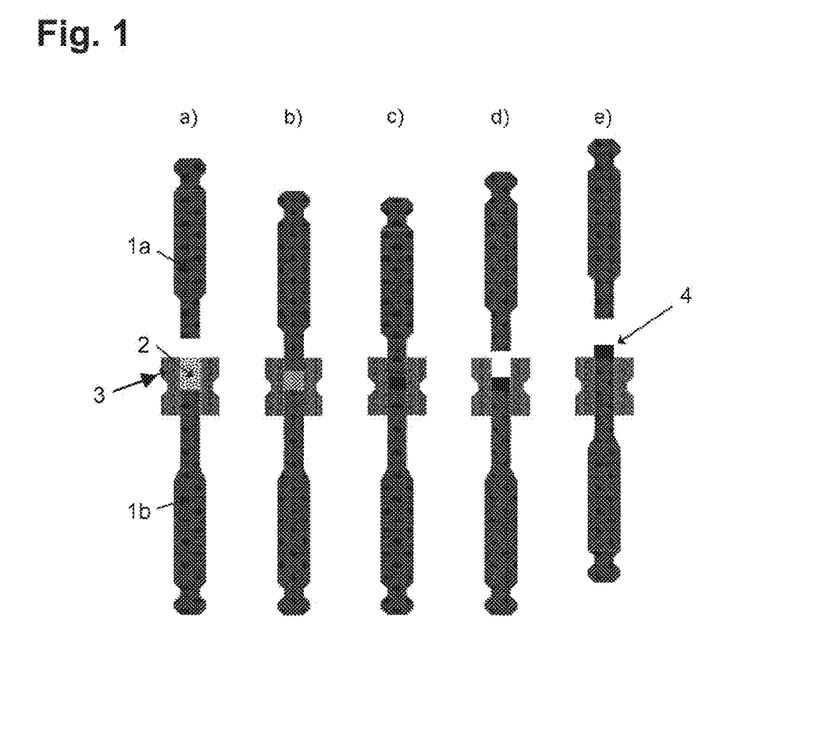
FIG. 1 shows a simplified schematic diagram of the tablet pressing operation.

FIG. 1 shows schematically the process for producing a tablet. The powder 2 to be pressed is a mixture of powdered constituents placed in a compression mold 3. Two axially aligned compression rams 1a, 1b exert mechanical forces axially, thus forming the tablet.

The diffractive microstructure to be created on the tablet is provided on the surface of the compression ram 1a, 1b and/or on the inside wall of the compression mold 3. If the wall of the compression mold 3 has a linear diffractive grating as the microstructure, then to support the ejection of the finished tablet 4, the grating lines are preferably arranged parallel to the axial direction of movement of the compression ram dies. It is simpler with regard to the mechanical stresses occurring in the compression process to apply the microstructure to the compression rams 1a, 1b.

The powder fills the cavity in the compression mold 3, which is sealed by the lower compression ram 1b (see FIG. 1(a)). The volume of the compression mold defines the quantity of powder that is compressed to form the tablet. This volume can be adjusted through the position of the lower compression ram 1b during the filling of the cavity. The compression force is typically between 5 and 25 kN. Modern rotary presses achieve maximal compression forces of up to 160 kN. During the compression process, two interrelated phenomena take place simultaneously: compression and consolidation (K. Marshall, "Tablet press fundaments," *Tablets & Capsules* 2005, pp. 6-11). The former leads to a reduction in the volume of the mass, while the latter causes an increase in the mechanical strength of the mass. Then when a force is applied to the powder, first its volume is reduced because the air between the particles is displaced (see FIG. 1(b)). This phase is known as the "repacking phase" and is limited by reaching the highest possible packing density and/or by friction at the contact points of the powder particles. Then most materials undergo elastic deformation up to the limit of plasticity (see FIG. 1(c)). This phase is known as the "squeezing phase." The particles may also experience brittle fractures due to the reduction in volume. Following this phase, the components may undergo plastic and/or viscoelastic deformation.

The diffractive microstructure is introduced into the tablet surface mainly by this plastic and/or viscoelastic deformation. Many materials used for pressing tablets, such as some polymers that are used as binders, have viscoelastic properties. If the surface of the particles is coated with a plastic material, the plasticity of a powder can be further improved. Particles can be partially coated with a binder, such as polyvinyl pyrrolidone (PVP), such as in moist granulation, thereby improving the compressibility of the particles. Because of particle-particle interactions, the mechanical resistance force of the tableting mass becomes progressively greater, the greater the applied compression force. In particle-particle interactions, bonds are formed at the particle surfaces because the number of contact points increases. Depending on the chemical composition, the bonds are ionic or covalent bonds, dipole-dipole interactions and van der Waals forces. There is often a mixture of these bonds. In addition, liquid films may solidify. Solidification of liquid films may take place in two ways. First, when heat of friction at the points of contact results in softening or melting of an ingredient having a low melting point, the mechanical stress at this point is dissipated. The ingredient then hardens via a melt bond. Second, an ingredient at the contact points where there is a high stress may dissolve in the liquid film present at the surface of a particle. Here again, the mechanical stress is dissipated and the material recrystallizes to form a bond. If the hardening takes place close to the surface of the microstructured compression mold, then the softened, molten or dissolved ingredient supports the replication of the diffractive microstructure.

At the end of the tablet pressing process, the pressure is removed (FIG. 1(d)) and the finished tablet 4 is ejected (FIG. 1(e)). The subsequent elastic recoil is minimized to achieve a high mechanical stability of the tablet. The recipe is thus optimized.

For tablets with diffractive microstructures in their surfaces, a recipe that meets all the requirements of tablet production and still has a sufficiently high plastic deformability to be able to create the microstructure is required. As mentioned, the powder to be compressed is of a mixture of various substances having different functions. The amount of plastically deformable materials in the recipe is selected to be as high as possible, but the requirements of the end product as well as FDA standards are still met. The amount of microcrystalline cellulose or plastic binders such as PVP may be increased, for example, or these materials used instead of excipients that are equivalent except for having a lower plastic deformability.

Modern industrial tablet presses are high-performance machines capable of producing tablets at very high speeds. The production speed of ultramodern single rotary presses is approximately 30,000 to 300,000 tablets per hour. In addition, they must offer extreme reliability and precision because all tablets must meet strict specifications with regard to thickness, weight, hardness and shape. The machines as well as all their components must be compliant with GMP (good manufacturing practice) and FDA requirements.

Table 3 shows examples of speed-specific data for various tablet presses. Additional information can be found in N. A. Armstrong, "Considerations of Compression Speed in Tablet Manufacture," *Pharmaceutical Technology*, September 1990, pp. 106-114. The short compression time is sufficient to compress the powdered raw material into a hard tablet.

TABLE 3

| Type of press | Speed per compression mold | Lowering time for the last 5 mm | Holding time |
| --- | --- | --- | --- |
| Eccentric | 85 tablets/min | 68.6 ms | 0 ms |
| Small rotary press | 44 tablets/min | 61.4 ms | 10.84 ms |
| Large rotary press | 100 tablets/min | 26.7 ms | 3.94 ms |
| Large rotary press | 121 tablets/min | 19.1 ms | 3.16 ms |

The lowering time and the holding time together are approximately equal to or somewhat longer than the time required in roll-to-roll processes (R2R) to hot-emboss diffractive microstructures in polymer films. Such R2R processes are used to produce holograms for bank note security and work with polymer feed rates of approx. 100 m/min. The polymer substrate, the process parameters and the temperature are optimized for good replication of the microstructure.

By analogy with that, the compression process in the method of this invention is adapted to the requirements of microstructuring. Most pharmaceutical pills have a round shape. This facilitates the production process because the compression die is rotationally symmetrical and can rotate freely during the compression process. For creating a diffractive microstructure, however, it is advantageous if rotation of the compression ram is prevented to reduce the resulting shearing forces, in particular during separation of the die from the tablet, because while the compression ram is moving away from the surface of the tablets, the tablet and the die surfaces may remain in contact for a short period of time due to elastic recoil.

Protecting the Microstructured Tablet Surface from Mechanical Damage

Figure 3:
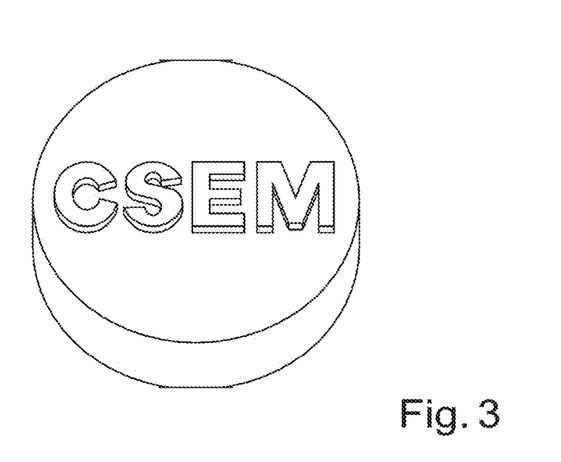
FIG. 3 shows a photograph of a pressed tablet with a diffractive microstructure produced by the method of this invention.
Figure 3A:
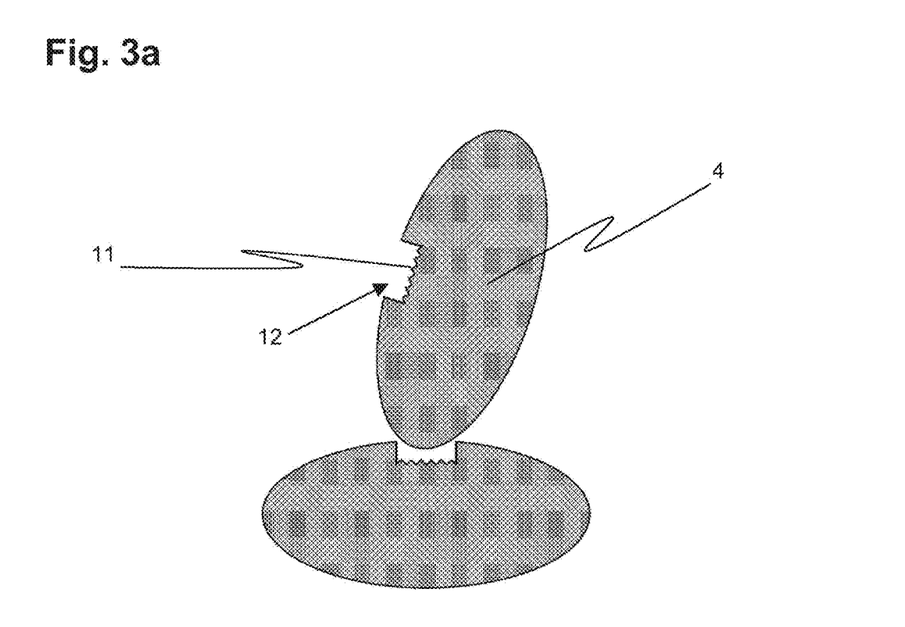
FIG. 3(a) shows a schematic diagram of the inventive tablets with microstructures in recesses.

To protect the microstructure during the entire product life cycle from mechanical effects, in particular from abrasive forces, the contact between the microstructured surface and other surfaces can be minimized, for example, by arranging the diffractive microstructure 11 in a macroscopic recess 12 in the surface of the tablet 4 (see FIG. 3(a)).

Such macroscopic recesses 12 are customary with the conventional direct tableting process. They are mainly used for marketing purposes to show, for example, the logo of the company, and the like. If the recess 12 is deep enough and small enough so that the sharpest edge of another pill cannot touch the microstructured surface (see FIG. 3a)), then the diffractive structure is well-protected from mechanical damage. No abrasion may occur in collecting containers, sorting machines or storage bottles. Recesses that are not as deep do not offer as much protection, but are occasionally unavoidable due to design requirements.

Alternatively or additionally, the microstructured tablets may be coated with an additional protective layer without destroying the diffractive effect, assuming the protective layer is transparent in the visible spectral range and has a refractive index that does not correspond to that of the material carrying the microstructure. Such a coating likewise protects the diffractive microstructure. If the refractive index of this coating is higher, the thickness is below 1 μm and the grating period of the microstructure is less than 500 nm, then diffractive color effects of the zero order may be achieved. These color effects are extremely counterfeit-proof and are easy to recognize.

Figure 4A:
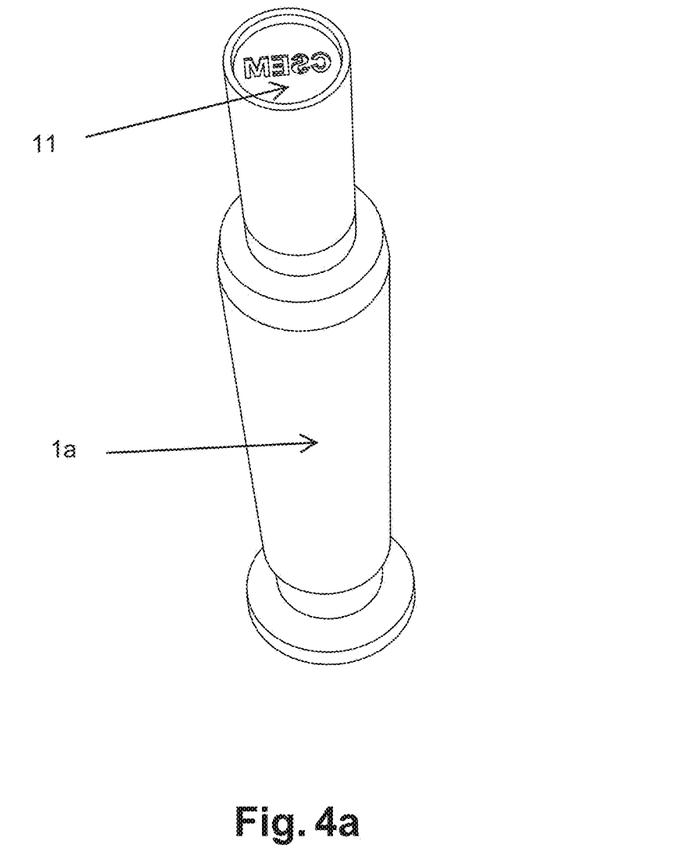
FIG. 4(a) shows a photograph of a microstructured compression die for use in the method of this invention and FIG. 4(b) shows an SEM micrograph (SEM=scanning electron microscope) of a table produced by the method of this invention.
Figure 4B:
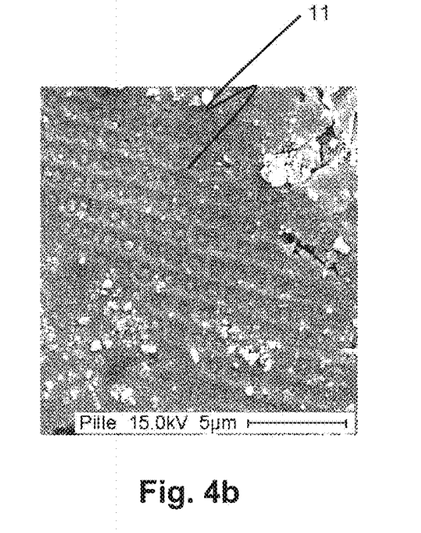

Example of an Inventive Pharmaceutical Tablet with a Diffractive Microstructure A powder mixture formulated according to Table 1 was compressed in a simple rotary press of the type 1200i from the company Fette, Germany with 24 compression ram pairs to form tablets. The compression rams had a diameter of 11.8 mm and a hard chrome-plated surface. A diffractive microstructure with a period of 1.4 μm and a depth of approx. 500 nm was ionically etched into the hard chrome-plated surface (see FIG. 4(a)). Visible diffractive effects in tablets with a weight of 540 mg were achieved with a compression force of 25 kN and a production speed of 30,000 tablets per hour. FIG. 3 shows one of the tablets produced in this way. The diffractive microstructure produces a clearly visible inscription "CSEM." The diffraction effects produced cannot be justifiably represented in the black-and-white photograph in FIG. 3. The hardness of the tablet is 154 N, which is a satisfactory value with respect to the dissolvability of the tablet. FIG. 4b shows an SEM micrograph of the microstructured surface of such a tablet. The diffractive microstructure is clearly visible.

Authentication of the Tablets of this Invention

If the tablets of this invention have a bright and/or luminous color, this strong background may make it difficult to recognize a rainbow effect in the diffractive microstructures. Because the usual powder components have a refractive index of approximately 1.5 in the visible spectral range, only a small percentage of the incident light on the tablet surface is reflected back in the first or higher diffraction orders. The angular distribution of the diffracted light is given by:

$$\Lambda(\sin \theta_m - \sin \theta_i) = m\lambda,$$

where $\theta_m$ is the angle of reflection of the m-th diffraction order, $\theta_i$ is the angle of incidence and $\lambda$ is the wavelength of the light (see FIG. 2(a)).

Because diffraction effects of a higher order are weaker, detection of the typical diffraction pattern may not be entirely simple for a layperson. The deep reflected intensity is not a disadvantage, however, because strong diffractive color effects could irritate the end consumer. Many patients are afraid of strongly colored pills. On the other hand, the visibility of the diffraction effect can easily be increased by suitable lighting with an optimized angle of incidence. This makes the effect a so-called security feature of the second level. In the pharmaceutical industry, second- or third-level security features are widespread because the corporations do not necessarily want to reveal to their end consumers that counterfeiting is a problem. Under exposure from a white LED, for example, the rainbow effect of the diffractive microstructure lights up at a certain angle of observation. With some practice, a person can check for the presence of the diffractive microstructure in less than one second with the help of such a verification device.

Figure 3B:
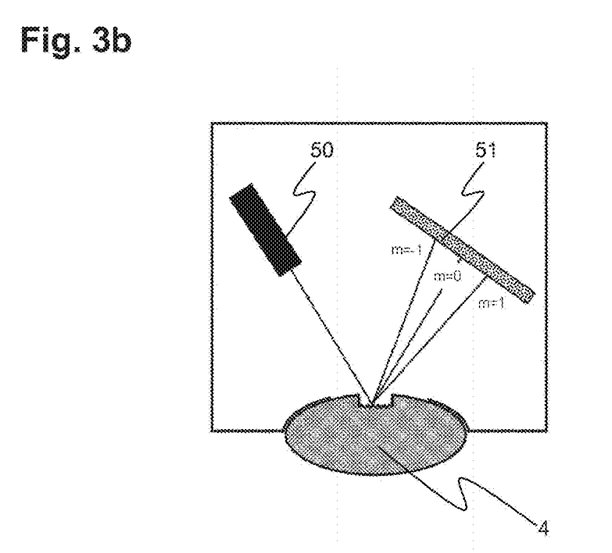
FIG. 3(b) shows a schematic diagram of a reading device for authentication of inventive tablets.

Checking for the presence of a diffractive microstructure is a qualitative authentication. A rapid and simple method of quantitative checking of diffractive microstructures includes exposing the structures with the beam of a laser diode (for example $\lambda=650$ nm) at a fixed angle of incidence. The laser beam is diffracted in the various diffraction orders according to the formula given above. Because the laser wavelength $\lambda$ and the angle of incidence $\theta_i$ are known, the period $\Lambda$ of the microstructure can be determined by measuring the diffraction angle of at least one order. This is done, for example, with the help of a portable reading device, which has a recess in which the pill is secured, ensuring a fixed angle of incidence of the laser beam (see FIG. 3(b)). The diffracted laser beams are collected by an array of photodiodes and the period of the microstructure is calculated on the basis of the positions of the diffracted rays. Such mobile reading devices may be used in pharmacies or by customs officials, for example.

Producing a Compression Die According to this Invention

To ensure a long lifetime, the material of the die carrying the microstructure must be very hard. At the same time, however, it must be possible to provide the microstructure in its surface. Suitable materials include, for example, hardened steel, hard chrome-plated steel, tungsten carbide or molybdenum carbide. All of these materials have been approved by the FDA and may be used for the compression rams or the compression molds. However, these materials are not compatible with the traditional holographic and lithographic techniques, but they can be microstructured by using other methods which are described below.

Ion Etching

Figure 5:
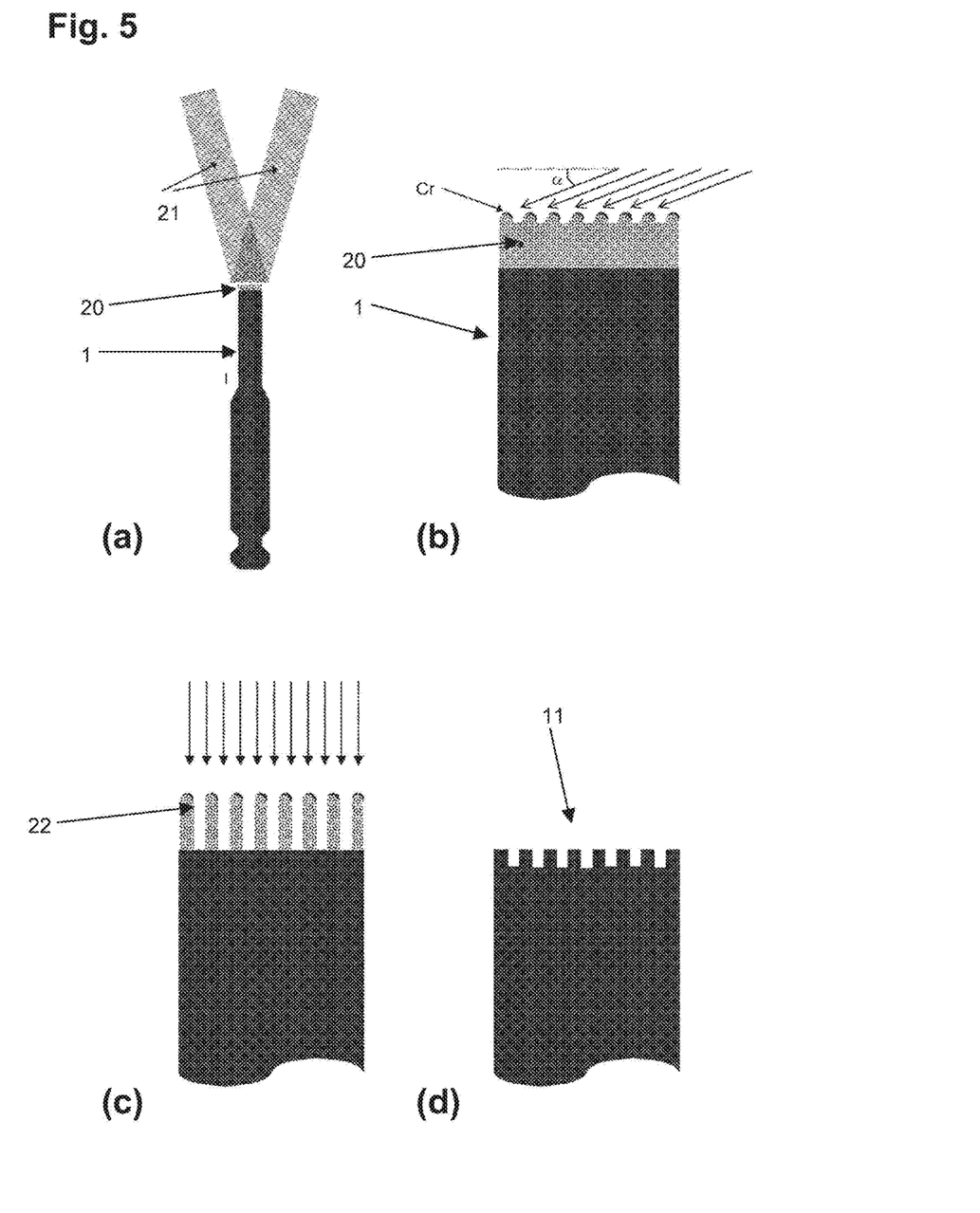
FIGS. 5(a)-5(d) show schematically the steps of the ion etching method for producing a compression die according to: (a) holographic lighting, (b) oblique chromium sputtering, (c) dry etching, and (d) finished microstructured compression die surface.

Hardened steel, steel with a hard chrome coating, tungsten carbide or molybdenum carbide may be microstructured with a special ionic etching technique. This technique comprises the following steps, which are diagrammed schematically in FIGS. 5(a) to 5(d):

1. A thin light-sensitive layer 20, a so-called photo-resist, is applied to the microstructured surface of the compression die. In FIG. 5(a), this is a compression ram 1. The coating is performed in a special room without blue radiation or UV. Suitable photoresist materials include, for example, ma-N440 (MRT) Microposit S1800 (Röhm & Haas) and AZ1500 (Clariant). The optimal thickness of layer 20 is in the range of 300 nm to 2000 nm. If the die is secured appropriately, the coating may be applied by spin coating (Convac 1001s) or by spray coating (EFD MicroCoat MC780S). The latter must be optimized for good homogeneity in the desired thickness range. After coating, the layer is hardened for 1-60 minutes, depending on the thickness and the material of the layer at 100° C. to 120° C., a so-called soft bake.

2. As the next step, the photoresist layer 20 is exposed using two interfering laser beams 21 in a holographic exposure (see FIG. 5(a)). Crossed gratings are implemented by two orthogonal exposures. The integrated performance is controlled by a photodiode and depends on the photoresist material and the desired grating parameters. The laser is, for example, an HeCd laser with a wavelength of $\lambda=441.6$ nm. Depending on the angle of incidence $\Theta$ of the two beams as well as the optical components of the holographic setup used, grating periods $\Lambda$ of 270 nm to 16,000 nm are possible, $\Lambda=\lambda/(2n \sin \Theta)$, where n is the refractive index of the material through which the laser beams expose the photoresist surface. If the exposure takes place in air, then n=1. Shadow masks may be used to define the shape of the grating surface. This makes it possible, for example, to implement logos, trademarks, etc.

3. After the exposure, the photoresist layer is developed in a suitable developing solution. For example, the basic developer S303 (Microposit) or concentrate (Microposit) may be used for this purpose. The developing time depends on the grating parameters to be established. Immediately after developing, the die is placed in a stop bath with pure water. The temperatures of the two baths are 30° C. and are monitored at ±0.2° C. At the end of the developing step, the photoresist layer on the pill compression die has a grating with the desired period and depth (see FIG. 5(b)). The shape may be sinusoidal, as already shown, or may be more complex.

4. To be able to dry etch the grating in the die surface, a contrast of at least 2:1 must be achieved in the etching rate. This is achieved by applying a metal hood, preferably a chromium hood with a bulk thickness of 10 nm to 200 nm to the elevated sides of the grating to which the photoresist layer 20 is applied. The optimal thickness depends on the grating depth and period. The tablet compression die with the developed photoresist layer 20 is arranged in a vacuum chamber (Balzers BAK550) so that the vaporized atoms are unable to reach the recesses in the grating. This oblique sputtering is diagrammed schematically in FIG. 5(b). The angle of incidence $\alpha$ of the metal atoms here is between 3° and 45°, depending on the grating depth and period. If necessary, oblique sputtering is performed from two or more sides to form symmetrical metal caps.

5. Then the photoresist layer 20 is opened, thus forming a mask 22. As shown in FIG. 5(c), the parts of the polymer resist layer are then etched with $O_2$ plasma (Oxford RIE) without chromium caps. The kinetic energy of the reactive oxygen ions is in the range of 500 eV. The etching rate also depends on the pressure in the vacuum chamber. The end of this opening step is defined by an end point detection system, which is based on laser interferometry.

6. The opened mask 22 is then used to transfer the grating structure 11 into the die surface by another dry etching step. This etching into the hard surface of the pill compression die is performed by bombarding it with argon ions (Veeco RF 350) with a kinetic energy on the order of magnitude of 500 eV. At 500 eV, the energy is low enough to prevent a great depth of penetration of the source ions into the sample but without reducing the etching rate. Table 4 shows typical etching rates r for such an argon bombardment at an ionic current density of 1 $mA/cm_2$, a kinetic energy of the ions of 500 eV and with perpendicular bombardment for various elements and compounds.

TABLE 4

| Element or compound | Argon etching rate r (nm/min) |
|---|---|
| Al | 73 |
| C | 4.4 |
| Cr | 58 |
| Cu | 110 |
| Fe | 53 |
| Mo | 54 |
| Ni | 66 |
| Si | 38 |
| SiC | 35 |
| $SiO_2$ | 40 |
| Ta | 42 |
| TaC | 10 |
| Ti | 38 |
| V | 37 |
| W | 38 |
| Zr | 62 |

If the desired grating depth has been reached, the remaining chromium and photoresist material are removed, leaving behind the finished microstructured surface of the inventive compression die (see FIG. 5(d)).

For an inexpensive production of the diffractive microstructures on the inventive compression dies, several such dies are produced in parallel in the most time-consuming steps, namely oblique sputtering and dry etching.

With the previously mentioned ionic etching method, coated compression dies can also be microstructured, for example hard chrome electroplating. FIG. 4(a) shows an illustration of an inventive compression ram 1(a) with a hard chrome electroplated surface. According to the method described above, a diffractive microstructure 11 is created in the surface. FIG. 4(b) shows an SEM micrograph of the microstructured surface of a tablet pressed using this compression die.

Embossing

Another method of creating a diffractive microstructure on an inventive compression ram includes hammering the desired microstructure into the surface of the inventive compression die by an embossing method using a main die. This main die can be microstructured with the ionic etching method described above.

It is known that macroscopic structures, such as chassis numbers or brand names can be hammered into metal. In the smallest case, such structures are typically a few millimeters in size. The required precision in structuring is low because the only requirement is that the numbers and letters must be legible. Hammering diffractive microstructures with periods on the order of 1 μm into inventive compression dies is of course much more complicated. The required precision is very high in order to obtain the interference effect in the microstructures. In addition, the microstructures are smaller than the internal structures of metals (grain size) and the dies are made of very hard metal alloys.

To facilitate an understanding of this method, a few characteristic mechanical properties of metals are summarized below. Metals tend to have a high melting point because of the strength of the metallic bond. The bond strength varies from one metal to the next and depends on, among other things, the number of electrons which each atom releases into the so-called free electron gas. In addition, it depends on the packing density. Each metal consists of a plurality of individual grains and/or crystallites, such as perfectly ordered microcrystalline regions. The average diameter of such grains is typically between 10 μm and 100 μm. The atoms at the grain boundaries, also known as dislocations, are also improperly aligned. Special treatments allow larger grain sizes and thus harder metals.

If a low mechanical stress acts on a metal, individual metal layers begin to slide over one another. As soon as the stress is removed, the atoms fall back into their original position, elastic deformation. If the stress is greater, the atoms slide into a new position and the metal is permanently deformed, plastic deformation. The movement of the dislocations causes a limited number of atomic bonds to be broken. The force required to break the bonds of all the atoms in a crystal plane simultaneously is very high. The movement of the dislocations, however, allows the atoms in crystal planes to slide by one another with much lower stresses. The energy required for such movement is the lowest along the densest crystal planes, so the dislocations within a metal grain have a preferred direction of movement. This leads to sliding dislocations along parallel planes within the grain. The diameter of such sliding lines is typically in the range of 10 nm to 1000 nm. The sliding lines are grouped and form sliding line stripes. The latter are visible even under an optical microscope. As described below, the sliding lines and sliding line stripes support the replication of microstructures. The displacement of atomic layers over one another is hindered by grain boundaries, which can be attributed to an unsuitable constellation of rows of atoms. Thus, the more grain boundaries there are in a piece of metal, for example, the smaller the individual crystal grains, the harder is the metal. The grain boundaries are regions where the atoms are not in good contact with one another, so metals tend to break at grain boundaries. The metal is thus not only harder due to the increase in the number of grain boundaries but also becomes more breakable.

The harder a metal, the more difficult it is to shape. Table 5 lists the Vickers hardness (HV), the material density ρ and the modulus of elasticity or Young's modulus E for various materials, not only metals and alloys.

TABLE 5

| Material | ρ (g/cm$^2$) | Hardness (HV) | E (GPa) | $\sigma_y$ (MPa) | $\sigma_u$ (MPa) |
| --- | --- | --- | --- | --- | --- |
| Diamond (C) | 3.52 | 10,060 | 1000 | — | — |
| Polycrystalline diamond/diamond-like carbon DLC (C) | 2.8-4.1 | 3000-12,000 | 150-800 | — | — |
| Cubic boron nitride (c-BN) | 3.48 | 4500 | 680 | — | 50 |
| Silicon carbide (SiC) | 3.22 | 3300 | 480 | — | 140 |
| Boron carbide (B$_4$C) | 2.5 | 3200 | 450 | — | 380 |
| Titanium carbide (TiC) | 4.93 | 3200 | 460 | — | 330 |
| Vanadium carbide (VC) | 5.4 | 2940 | 420 | — | — |
| Aluminum nitride (AlN) | 3.2 | 2500 | 350 | — | 500 |
| Tungsten carbide (W$_2$C) | 15.6 | 2400 | ≈700 | — | 530 |
| Titanium nitride (TiN) | 5.22 | 2100 | 260 | — | — |
| Corundum (Al$_2$O$_3$) | 3.97 | 2060 | ≈400 | — | 320 |
| Molybdenum carbide (Mo$_2$C) | 8.2 | 1950 | 550 | — | — |
| Tantalum carbide (TaC) | 13.9 | 1800 | ≈340 | — | — |
| Silicon nitride (Si$_3$N$_4$) | 3.2 | 1400-1700 | ≈340 | — | 580 |
| Zirconium oxide (ZrO$_2$) | 5.6 | 1400-1600 | 240 | — | 1000 |
| Chromium (Cr) | 6.9-7.2 | 750-1050 | 289 | 360 | 690 |
| Hardened nickel | 7.9-8.1 | 600-950 | 214 | — | — |
| Hardened steel | ≈7.8 | 500-900 | 190-214 | 520 | 860 |
| Nickel | 8.91 | 550 | 214 | 940 | 1010 |
| Unhardened steel | ≈7.8 | 100-500 | 190-214 | 365 | 900 |
| Aluminum | 2.7 | 25 | ≈70 | 260 | 290 |

Figure 6:
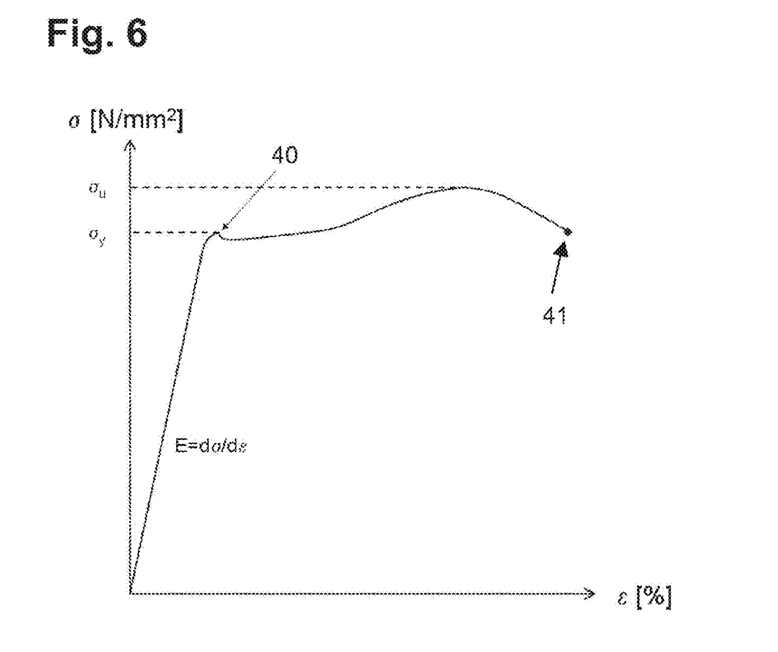
FIG. 6 shows a graph of an example of a stress-strain curve.

The modulus of elasticity does not depend on the degree of hardness. The hardness is a measure at which plastic deformation begins due to mechanical stress. Young's modulus $E=d\sigma/d\epsilon$ is the slope of the linear portion of the stress-strain curve $\sigma(\epsilon)$. FIG. 6 shows an example of such a curve for a ductile material such as steel. The greater the resistance of a material to elastic deformation, larger is the value of Young's modulus. Plastic deformation takes place above the elastic limit (40). The yield point $\sigma_y$ measures the resistance to plastic deformation. Any increase in stress above the yield point (40) causes permanent deformation of the material. In this so-called flow zone, deformation is relatively great even with a slight increase in stress. This process, which is often characterized by a very low slope of the stress-strain curve, is often referred to as "perfect plasticity." After flowing, this stress is increased up to the breaking strength or ultimate tensile stress $\sigma_u$ at which the material breaks (41). In the case of breakable materials, the flow zone practically does not exist at all. Breakable materials in comparison with ductile materials often have a relatively high Young's modulus and ultimate tensile stress. Table 5 lists the maximum values for $\sigma_y$ and $\sigma_u$. All the values in Table 5 are merely reference values. The data from proper samples may deviate from this considerably. Values of coatings of such materials depend on the process parameters and the growth mechanism, among others.

To be able to hammer a diffractive microstructure with a main die into an inventive compression die, the following prerequisites are met:

1. The hardness of the main die is greater than that of the compression die.

2. Young's modulus is as high as possible for both in order to minimize the elastic deformation.

3. The applied stress must be higher than the yield point but lower than the ultimate tensile stress of the compression die. Furthermore, it must be lower than the yield point, if any, and the ultimate tensile stress of the main die.

If necessary, the compression mold or its surface may be hardened after hammering in the microstructure by a subsequent heat treatment or ion implantation.

Figure 8:
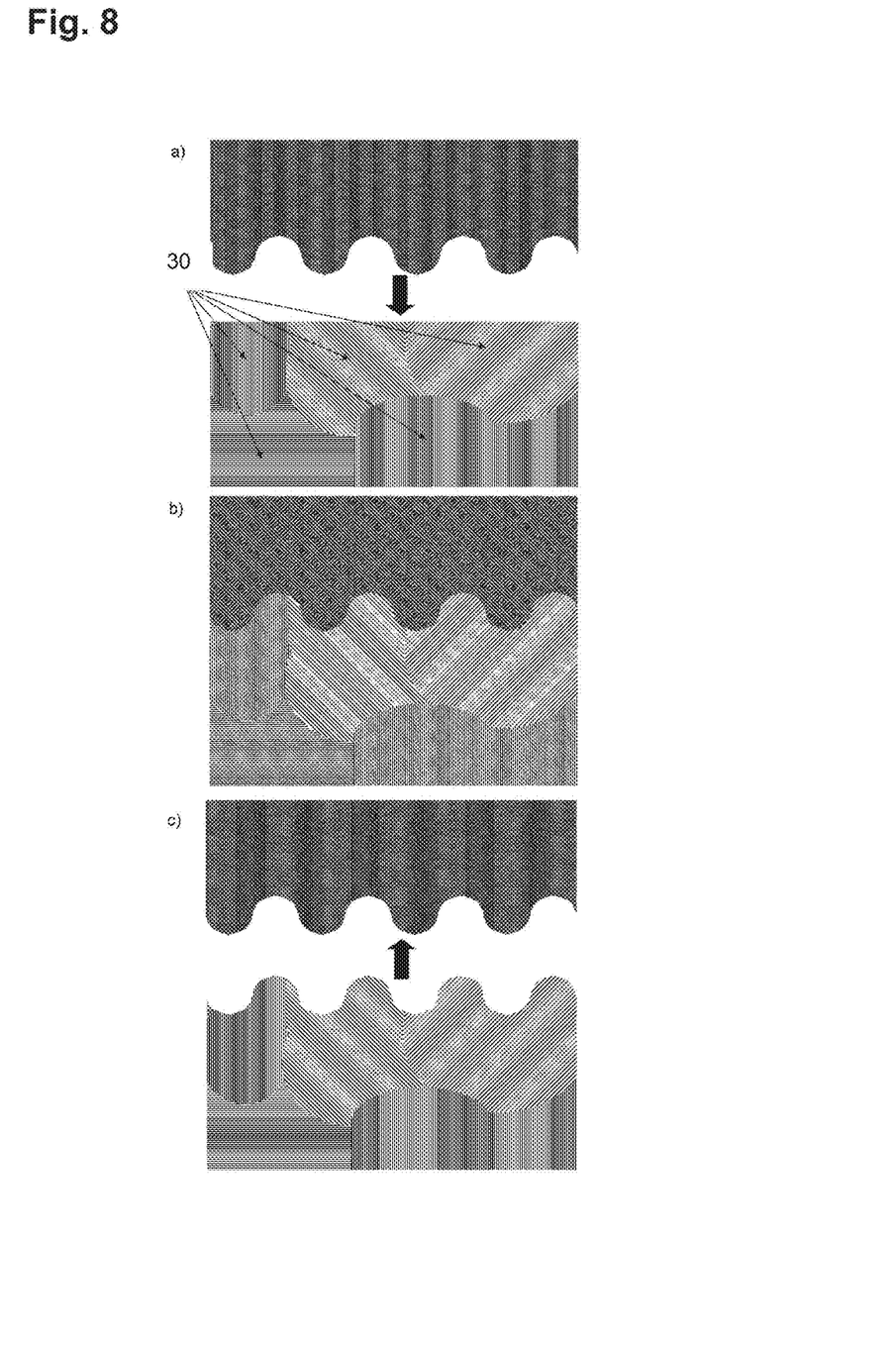
FIGS. 8(a)-8(c) each shows a schematic diagram of a hammering process to illustrate a diffractive microstructure on a compression die surface.

FIG. 8 shows schematically how the microstructures of the main die in the embossing step are replicated by filling the cavities through the sliding planes in the metal grains on the compression die.

To be able to microstructure a compression die with an electroplated hard chrome surface, a main die of tungsten carbide, for example, is necessary and an embossing force of approximately 400-500 MPa is required. As an alternative to that, the main die may also be made of hardened steel with a coating of tungsten carbide, $Si_3N_4$ or $ZrO_2$, for example, which carries the microstructure. The latter embodiment is less expensive because only the coating must be made of the very hard and fracture-resistant material.

Figure 7:
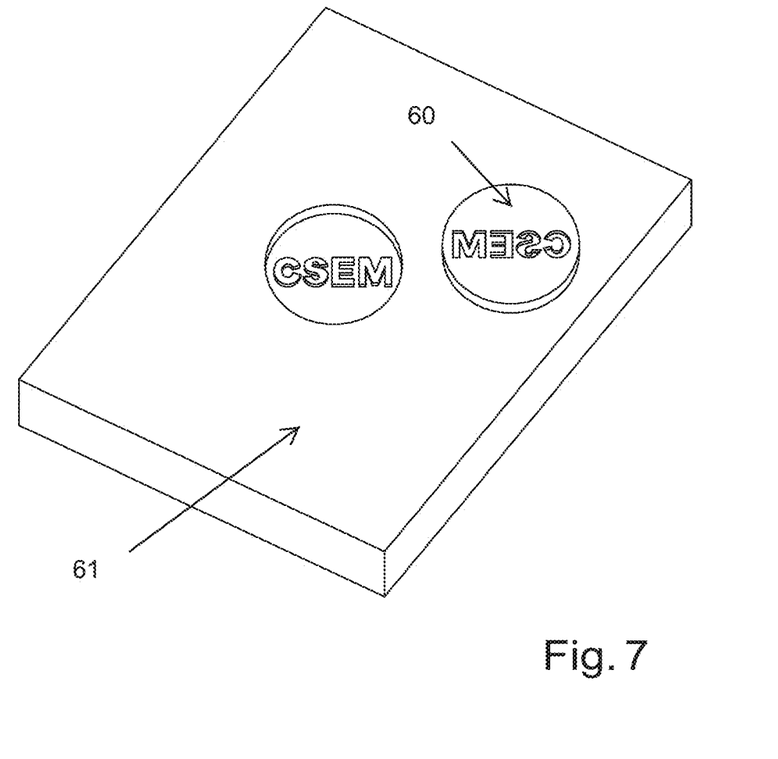
FIG. 7 shows a photograph of an aluminum plate microstructured by cold embossing.

FIG. 7 shows an example of a microstructure produced with such an embossing method on a metal surface. A block of aluminum 61 with a thickness of approximately 4 mm was microstructured using a round nickel shim 60 with a diameter of approximately 12 mm. The nickel shim 60 is resting on the metal block 61 in FIG. 7. The shim 60 has a diffractive grating with a period of 1400 nm and a depth of approx. 300 nm which shows the four letters CSEM in mirror image. The shim 60 was pressed onto the aluminum block for approximately 0.5 sec under a pressure of 3 tons at room temperature. As FIG. 7 shows, the diffractive microstructure was reproduced well on the aluminum block.

The invention claimed is:

1. A tablet at least for pharmaceutical use, the tablet comprising:
   a plurality of individual powder particles;
   a macroscopic recess in the surface of the tablet;
   diffractive microstructures embossed on surfaces of the powder particles situated on a recessed surface of said macroscopic recess, the diffractive microstructures being contained within said macroscopic recess;
   a refractive coating formed over the diffractive microstructures;
   wherein the diffractive microstructures and coating are configured to provide zero order diffractive microstructures that exhibit zero order diffractive color effects, and
   wherein said macroscopic recess is sufficiently deep and narrow such that the smallest edge from another substantially identical tablet cannot touch said diffractive microstructures.

2. The tablet according to claim 1, wherein the grating microstructure has a relief with an essentially triangular or sinusoidal profile.

3. The tablet according to claim 2, wherein the grating microstructures are linear gratings or hole-raster gratings.

4. The tablet according to claim 3, wherein a period length A of the grating microstructure is less than or equal to 500 nm.

5. The tablet according to claim 4, wherein a depth t of the relief between the grating lines of the grating microstructure is at least 80 nm.

6. The tablet according to claim 5, wherein the depth t of the relief between the grating lines of the grating microstructure is a maximum of 1000 nm.

7. The tablet according to claim 6 wherein the depth t of the relief between the grating lines of the grating microstructure is between 0.3 and 0.4 period lengths A of the grating microstructure.

8. The tablet according to claim 1, wherein the refractive index of the coating is higher than the refractive index of the tablet material, and the thickness of the coating is less than 1 µm.

9. A tablet comprising:
   powder particles compressed into a shape comprising an edge, an outer surface and a recessed surface below said outer surface;
   said recessed surface comprising diffractive microstructures embossed on said powder particles on the recessed surface, said diffractive microstructures being grating microstructures having a depth of the relief between grating lines of at least 80 nm to a maximum of 1000 nm;
   said recessed surface being located in a macroscopic recess that is sufficiently deep and narrow such that said diffractive microstructures are contained within said macroscopic recess and such that an edge from another substantially identical tablet is not able to contact said diffractive microstructures;
   a refractive coating being formed over the diffractive microstructures;
   wherein the diffractive microstructures and coating are configured to provide zero order diffractive microstructures that exhibit zero order diffractive color effects.

* * * * *